US011583662B2

(12) United States Patent
Jaski

(10) Patent No.: US 11,583,662 B2
(45) Date of Patent: Feb. 21, 2023

(54) METHODS AND COMPOSITIONS FOR CONSISTENT INTRACORONARY ADMINISTRATION OF A BIOLOGIC

(71) Applicant: Sardocor Corp., Lexington, MA (US)

(72) Inventor: Brian Jaski, San Diego, CA (US)

(73) Assignee: Sardocor Corp., Lexington, MA (US)

( * ) Notice: Subject to any disclaimer, the term of this patent is extended or adjusted under 35 U.S.C. 154(b) by 316 days.

(21) Appl. No.: 15/490,202

(22) Filed: Apr. 18, 2017

(65) Prior Publication Data

US 2017/0296790 A1  Oct. 19, 2017

Related U.S. Application Data

(60) Provisional application No. 62/323,937, filed on Apr. 18, 2016.

(51) Int. Cl.
| *A61M 25/06* | (2006.01) |
| *A61M 5/142* | (2006.01) |
| *A61L 31/16* | (2006.01) |
| *C12N 15/86* | (2006.01) |
| *A61K 48/00* | (2006.01) |
| *A61K 31/04* | (2006.01) |
| *A61K 38/46* | (2006.01) |
| *A61L 29/04* | (2006.01) |
| *A61L 29/06* | (2006.01) |
| *A61L 29/16* | (2006.01) |
| *A61M 5/00* | (2006.01) |
| *A61M 5/14* | (2006.01) |
| *A61M 25/00* | (2006.01) |
| *C12N 7/00* | (2006.01) |

(52) U.S. Cl.
CPC .......... *A61M 25/0662* (2013.01); *A61K 31/04* (2013.01); *A61K 38/46* (2013.01); *A61K 48/00* (2013.01); *A61K 48/005* (2013.01); *A61K 48/0075* (2013.01); *A61L 29/041* (2013.01); *A61L 29/042* (2013.01); *A61L 29/06* (2013.01); *A61L 29/16* (2013.01); *A61L 31/16* (2013.01); *A61M 5/007* (2013.01); *A61M 5/14* (2013.01); *A61M 5/142* (2013.01); *A61M 25/0043* (2013.01); *C12N 7/00* (2013.01); *C12N 15/86* (2013.01); *C12Y 306/03008* (2013.01); *A61L 2300/252* (2013.01); *A61L 2300/442* (2013.01); *A61L 2400/06* (2013.01); *A61L 2430/20* (2013.01); *A61M 2005/1403* (2013.01); *A61M 2202/04* (2013.01); *A61M 2202/0468* (2013.01); *A61M 2202/206* (2013.01); *C12N 2750/14143* (2013.01)

(58) Field of Classification Search
CPC .......... A61M 25/0662; A61M 25/0043; A61M 5/142; A61M 5/007; A61M 5/14; A61M 2202/0468; A61M 2202/04; A61M 2202/206; A61M 2005/1403; A61K 31/04; A61K 38/46; A61K 48/00; A61L 29/041; A61L 29/042; A61L 29/06; A61L 29/16

See application file for complete search history.

(56) References Cited

U.S. PATENT DOCUMENTS

| 5,702,372 | A | 12/1997 | Nelson |
| 8,221,738 | B2 * | 7/2012 | Zsebo ................ A61K 48/0008 424/93.1 |
| 8,636,998 | B2 | 1/2014 | Zsebo |
| 2002/0156434 | A1 | 10/2002 | Van Antwerp |
| 2008/0076730 | A1 | 3/2008 | Zsebo |
| 2008/0091140 | A1 * | 4/2008 | Hamburger ....... A61M 25/0108 604/93.01 |
| 2008/0140045 | A1 * | 6/2008 | Crank ................... A61M 39/12 604/403 |
| 2008/0215008 | A1 * | 9/2008 | Nance .............. A61B 17/12122 604/164.03 |

FOREIGN PATENT DOCUMENTS

EP   2044199   11/2012

OTHER PUBLICATIONS

Hulot, J.S., et al, Sarcoplasmic reticulum and calcium cycling targeting by gene therapy, Gene Therapy 16(6):596-599(2012) (Year: 2012).*
Yousef, A.E., Choice of guiding catheters and guidewires, May 19, 2014 [retrieved from internet on May 23, 2017] <URL: www.cardioegypt.com/cardioeg/ACSCA2014-Presentations/004001.pdf> (Year: 2014).*
Hulot, J.S., et al., Sarcoplasmic reticulum and calcium cycling targeting by gene therapy, Gene Therapy 16(6):596-599 (2012).
Karakikes, I, et al., Concomitant Intravenous Nitroglycerin with Intracoronary Delivery of AAV1.SERCA2a Enhances Gene Transfer in Porcine Hears, Molecular Therapy, 20(3):565-571 (2012).
Written Opinion of the International Searching Authority and Search Report issued in Application No. PCT/US2017/028152 dated May 26, 2017.

(Continued)

*Primary Examiner* — Nathan R Price
*Assistant Examiner* — Anh Bui
(74) *Attorney, Agent, or Firm* — Knobbe, Martens, Olson & Bear LLP

(57) ABSTRACT

Some embodiments provided herein relate to methods, systems and kits for providing consistent intracoronary administration of a biologic to subjects having diverse coronary anatomies. In some embodiments, the biologic is an adeno-associated virus serotype 1 (AAV1) vector encoding sarcoplasmic/endoplasmic reticulum ATPase 2a (SERCA2a) protein.

26 Claims, No Drawings

(56) References Cited

OTHER PUBLICATIONS

Yoursef, A.E., Choice of guiding catheters and guidewires, May 19, 2014 [retrieved from internet on May 23, 2017] <URL: www.cardioegypt.com/cardioeg/ACSCA2014-Presentations/004001.pdf>.

Zsebo K., et al., Long-term effects of AAV1/SERCA2a gene transfer in patients with severe heart failure, Circ. Res. 114:101-108 (2014).

\* cited by examiner

METHODS AND COMPOSITIONS FOR CONSISTENT INTRACORONARY ADMINISTRATION OF A BIOLOGIC

RELATED APPLICATIONS

This application claims the benefit of U.S. Provisional Application No. 62/323,937 filed Apr. 18, 2016, the contents of which is incorporated by reference in its entirety.

FIELD OF THE INVENTION

Some embodiments provided herein relate to methods, systems, and kits for providing consistent intracoronary administration of a biologic to subjects having diverse coronary anatomies. In some embodiments, the biologic is an adeno-associated virus serotype 1 (AAV1) vector encoding sarcoplasmic/endoplasmic reticulum ATPase 2a (SERCA2a) protein.

BACKGROUND OF THE INVENTION

One promising recent development in the treatment diseases, such as heart failure is the use of biologies, such as antibodies and viral vectors. Using such biologies and other therapies, the treatment of heart failure can tailored to the individual patient, based on the underlying causes, comorbidities and the patient's stage at diagnosis and New York Heart Association (NYHA) functional classification. Treatment goals include the reduction of symptoms, prolongation of survival, improvement to the quality of life, and inhibition of disease progression. Despite optimal medical therapy employing a wide range of pharmacologic, device and surgical therapeutic options, over the long-term, most patients experience a progressive decline to advanced heart failure refractory to optimal medical therapy, ultimately succumbing to the syndrome or one of the underlying contributing conditions.

However, along with these new biologic therapies come complications with their delivery to the patient, particularly where the biologic must be delivered via catheter into an organ of the patient, such as the heart or liver. There remains a need for consistent, predictable and safe methods of delivering these new therapies.

SUMMARY OF THE INVENTION

Some embodiments of the methods, systems and kits provided herein include a method for providing consistent intracoronary administration of a biologic to a plurality of subjects, wherein the plurality of subjects comprise diverse coronary anatomies comprising: (a) obtaining an infusion catheter having proximal and distal ends, wherein the infusion catheter is adapted for use in the intracoronary administration of the biologic to a subject, and wherein a contact surface of the infusion catheter comprises a material that is compatible with the biologic; (b) obtaining a guide catheter having proximal and distal ends, wherein the guide catheter is adapted for the coronary anatomy of a subject selected from a plurality of subjects comprising diverse coronary anatomies; (c) inserting the distal end of guide catheter into a coronary artery or vein of the subject and extending the infusion catheter through the length of the lumen of the guide catheter such that the distal end of the infusion catheter is flush with or extends from the distal end of the guide catheter; and (d) administering the biologic to cardiac tissue of the subject through the lumen of the infusion catheter. Some embodiments also include repeating steps (a)-(d) for an additional subject from the plurality of subjects, wherein the coronary anatomy of the subject and guide catheter adapted for the coronary anatomy of the subject in the subsequent iteration of step (b) are each different from the guide catheter and the coronary anatomy of subject of the first iteration of step (b), and wherein the contact surface material of the infusion catheter in the subsequent iteration of step (a) is the same as the contact surface material of the infusion catheter of the first iteration of step (a).

Some embodiments include a method for administering a biologic to cardiac tissue of a subject comprising: (a) obtaining an infusion catheter having proximal and distal ends, wherein the infusion catheter is adapted for use in the intracoronary administration of the biologic to a subject, and wherein a contact surface of the infusion catheter comprises a material that is compatible with the biologic; (b) obtaining a guide catheter having proximal and distal ends; (c) extending the infusion catheter through the length of the lumen of the guide catheter such that the distal end of the infusion catheter is flush with or extends from the distal end of the guide catheter; and (d) administering the biologic to the cardiac tissue through the lumen of the infusion catheter.

In some embodiments, the guide catheter is adapted for the specific coronary anatomy of the subject. In some embodiments the surface material of the guide catheter, for example lumen(s) of the guide catheter, has not been determined to be compatible with the biologic.

In some embodiments, the infusion catheter is government-approved for specific use with the biologic.

In some embodiments, the infusion catheter is adapted for insertion into any one of a plurality of different guide catheters.

In some embodiments, obtaining an infusion catheter further comprises determining the contact surface of the infusion catheter is compatible with the biologic. In some embodiments, obtaining an infusion catheter further comprises selecting an infusion catheter based on the contact surface of the infusion catheter being known to be compatible with the biologic.

In some embodiments, each guide catheter of the plurality is adapted for a different coronary anatomy of a subject.

Some embodiments also include selecting the guide catheter adapted for the specific coronary anatomy of the subject. In some embodiments, the coronary anatomy of the subject is selected from the group consisting of: non-obstructive or nonocclusive; occluded right coronary artery; occluded left anterior descending artery; occluded left circumflex artery; left dominant circulation; short or non-existent left main coronary artery, with right dominance; and short or non-existent left main coronary artery, with left dominance. In some embodiments, the coronary anatomy of the subject is selected from the group consisting of: non-obstructive or nonocclusive, with right or co-dominance; occluded right coronary artery, patent left coronary artery, left to right collaterals, with right or co-dominance; occluded left anterior descending artery, patent left circumflex artery, right to left collaterals from right coronary artery to left anterior descending artery, with right or co-dominance; occluded left circumflex artery, patent left anterior descending artery, right to left collaterals to left circumflex artery from right coronary artery, with right or co-dominance; left dominant circulation, with left dominance; short or non-existent left main coronary artery such that the anatomy allows for an operator to cannulate both the left anterior descending artery and left circumflex artery with a single or combination of catheters, with right dominance; and short or non-existent left main coronary artery such that the anatomy allows for an operator to cannulate both the left anterior descending artery and left circumflex artery with a single or combination of catheters, with left dominance.

In some embodiments, the guide catheter is adapted for delivery of the distal end of the infusion catheter to a left coronary artery, a right coronary artery, a left anterior descending artery, a left circumflex artery, a saphenous vein graft, or a left internal mammary artery graft. In some embodiments, the guide catheter is selected from the group consisting of diagnostic catheter, guide angiographic catheter for selective arterial engagement, guide angiographic catheter for selective venous engagement, and guide angiographic catheter for selective bypass graft engagement.

In some embodiments, a contact surface of the infusion catheter is coated with a hydrophilic material, a hydrophobic material, or a material known to be compatible with the biologic administered through the infusion catheter. In some embodiments, a contact surface of the infusion catheter comprises a material selected from the group consisting of polyurethane, polypropylene, polyvinyl chloride, polytetrafluoroethylene (Teflon®), nylon, polyurethane, nylon/polyurethane, polyethylene terephthalate stainless steel, polyether block amides (Pebax®), and thermoplastic rubber (Santoprene) and combinations thereof.

In some embodiments, the infusion catheter has an external diameter in the range from about 0.5 French to about 10 French.

In some embodiments, the lumen at the distal end of the infusion catheter has a diameter in the range from about 0.010 inches to about 0.040 inches.

In some embodiments, during administration of the biologic the lumen of the infusion catheter is in fluid communication with a delivery device selected from the group consisting of a syringe, a stopcock, a manifold, an infusion pump, sterile tubing, and an infusion line, wherein a surface of the delivery device contacting the biologic is compatible with the biologic.

In some embodiments, the surface of the delivery device contacting the biologic is government-approved for specific use with the biologic.

Some embodiments also include flushing a radiopaque dye through the guide catheter lumen external to the infusion catheter lumen, and from the distal end of the guide catheter.

Some embodiments also include intravenous administration of nitroglycerin to the subject. In some embodiments, the nitroglycerin is administered to the subject for a period of at least 10 minutes prior to administration of the biologic. In some embodiments, the nitroglycerin is administered during administration of the biologic.

In some embodiments, the biologic is administered into the lumen of a blood vessel of the coronary circulation in vivo. In some embodiments, the blood vessel is selected from a left coronary artery, a right coronary artery, a left anterior descending artery, and a left circumflex artery.

In some embodiments, the biologic is administered at a rate of about 0.1 ml/min to about 20 ml/min. In some embodiments, the biologic is administered at a rate of about 5 ml/min. In some embodiments, the biologic is administered in a single dose. In some embodiments, the biologic comprises a vector for gene therapy. In some embodiments, the biologic comprises an adeno-associated virus (AAV) vector. In some embodiments, the biologic comprises a therapeutic polynucleotide encoding a sarcoplasmic/endoplasmic reticulum ATPase 2a (SERCA2a) protein. In some embodiments, the biologic comprises about $2.5 \times 10^{14}$ DNase resistant particles (DRP) adeno-associated virus serotype 1 (AAV1) vector encoding sarcoplasmic/endoplasmic reticulum ATPase 2a (SERCA2a) protein. In some embodiments, the biologic comprises about 50 ml dose comprising a buffer, sodium chloride, L-histidine, magnesium chloride, polysorbate 20, and water. In some embodiments, the biologic comprises saline.

In some embodiments, the subject lacks AAV1 neutralizing antibodies. In some embodiments, the subject has cardiomyopathy. In some embodiments, the subject has ischemic cardiomyopathy. In some embodiments, the subject has advanced heart failure with systolic dysfunction. In some embodiments, the subject has New York Heart Association (NYHA) class III/IV symptoms of heart failure.

In some embodiments, the guide catheter lacks government approval for specific use with the biologic. Some embodiments also include obtaining government approval for the use of the infusion catheter in the administration of the biologic to cardiac tissue of the subject.

Some embodiments also include determining a binding of the biologic to a contact surface of the infusion catheter and/or delivery device(s). In some embodiments, the contact surface is determined to bind less than 1% of a dose of the biologic. In some embodiments, the contact surface material of the infusion catheter and/or delivery device(s) has a binding level of the biologic below a pre-determined level required for compatibility with the biologic. In some embodiments, the pre-determined level of binding for compatibility is less than 1% of a dose of the biologic. Some embodiments also include determining a degradation rate of the biologic contacting a contact surface of the infusion catheter and/or delivery device(s). In some embodiments, the contact surface is determined to degrade less than 1% of a dose of the biologic. In some embodiments, the contact surface material of the infusion catheter and/or delivery device(s) has a degradation level of the biologic below a pre-determined level required for compatibility with the biologic. In some embodiments, the pre-determined level of degradation for compatibility is less than 1% of a dose of the biologic. In some embodiments, a surface material of a lumen of the guide catheter has not been determined to be compatible with the biologic.

In some embodiments, the subject is mammalian. In some embodiments, the subject is human.

Some embodiments include a kit for providing consistent intracoronary administration of a biologic to a subject of a plurality of subjects, wherein the plurality of subjects comprise diverse coronary anatomies comprising: a biologic; and an infusion catheter adapted for specific use in the intracoronary administration of the biologic to a subject, and adapted for insertion into any one of a plurality of guide catheters, wherein each guide catheter of the plurality is adapted for a different coronary anatomy.

Some embodiments also include a guide catheter adapted for the coronary anatomy of a subject.

Some embodiments include a system for providing consistent intracoronary administration of a biologic to subject of a plurality of subjects, wherein the plurality of subjects comprise diverse coronary anatomies comprising: a biologic; a plurality of guide catheters, wherein each guide catheter is adapted for a different coronary anatomy of a subject; and an infusion catheter adapted for insertion into each of the plurality of guide catheters, and adapted for specific use in the intracoronary administration of the biologic to the subject.

Some embodiments also include a delivery device selected from the group consisting of a syringe, a stopcock, a manifold, an infusion pump, sterile tubing, and an infusion line, wherein a surface of the delivery device that contacts the biologic during administration is adapted for specific use with the biologic.

In some embodiments, the infusion catheter and surface of the delivery device are government-approved for specific use with the biologic. In some embodiments, the guide catheter lacks government-approval for specific use with the biologic.

In some embodiments, the biologic comprises a vector for gene therapy. In some embodiments, the biologic comprises an adeno-associated virus (AAV) vector. In some embodiments, the biologic comprises a therapeutic polynucleotide encoding a sarcoplasmic/endoplasmic reticulum ATPase 2a (SERCA2a) protein. In some embodiments, the biologic comprises about $2.5 \times 10^{13}$ DNase resistant particles (DRP) adeno-associated virus serotype 1 (AAV1) vector encoding sarcoplasmic/endoplasmic reticulum ATPase 2a (SERCA2a) protein. In some embodiments, the biologic comprises about 50 ml dose comprising a buffer, sodium chloride, L-histidine, magnesium chloride, polysorbate 20, and water. In some embodiments, the biologic comprises saline. In some embodiments, the biologic is lyophilized. Some embodiments also include a diluent compatible with the biologic.

In some embodiments, the coronary anatomy of the subject is selected from the group consisting of: non-obstructive or nonocclusive; occluded left anterior descending artery; occluded left circumflex artery; left dominant circulation; short or non-existent left main coronary artery, with right dominance; and short or non-existent left main coronary artery, with left dominance.

In some embodiments, the coronary anatomy of the subject is selected from the group consisting of: non-obstructive or nonocclusive, with right or co-dominance; occluded right coronary artery, patent left coronary artery, left to right collaterals, with right or co-dominance; occluded left anterior descending artery, patent left circumflex artery, right to left collaterals from right coronary artery to left anterior descending artery, with right or co-dominance; occluded left circumflex artery, patent left anterior descending artery, right to left collaterals to left circumflex artery from right coronary artery, with right or co-dominance; left dominant circulation, with left dominance; short or non-existent left main coronary artery such that the anatomy allows for an operator to cannulate both the left anterior descending artery and left circumflex artery with a single or combination of catheters, with right dominance; and short or non-existent left main coronary artery such that the anatomy allows for an operator to cannulate both the left anterior descending artery and left circumflex artery with a single or combination of catheters, with left dominance.

In some embodiments, a contact surface of the infusion catheter is coated with a hydrophilic material, a hydrophobic material, or a material known to be compatible with the biologic administered through the infusion catheter. In some embodiments, a contact surface of the infusion catheter comprises a material selected from the group consisting of polyurethane, polypropylene, polyvinyl chloride, polytetrafluoroethylene (Teflon®), nylon, polyurethane, nylon/polyurethane, polyethylene terephthalate stainless steel, polyether block amides (Pebax®), and thermoplastic rubber (Santoprene), and combinations thereof.

In some embodiments, the infusion catheter has an external diameter in the range from about 0.5 French to about 10 French.

In some embodiments, the lumen at the distal end of the infusion catheter has a diameter in the range from about 0.010 inches to about 0.040 inches.

In some embodiments, a contact surface of the infusion catheter and/or delivery device(s) bind less than 1% of a dose of the biologic. In some embodiments, a contact surface of the infusion catheter and/or delivery device(s) degrades less than 1% of a dose of the biologic. In some embodiments, a surface material of a lumen of the guide catheter has not been determined to be compatible with the biologic.

In some embodiments, the biologic is selected from the group of an antibody, including a fragment and/or derivative thereof, a vaccine, blood, one or more blood components, a somatic cell, a tissue, a proteins, a recombinant protein, a nucleic acid, a vector for gene therapy, a viral vector, and a combination of one or more of the preceding.

DETAILED DESCRIPTION

Some embodiments provided herein relate to methods, systems, and kits for providing consistent administration of a biologic. In some embodiments, the methods, systems, and kits provide for consistent intracoronary administration of the biologic to subjects having diverse coronary anatomies. In some embodiments, the biologic is an adeno-associated virus serotype 1 (AAV1) vector encoding sarcoplasmic/endoplasmic reticulum ATPase 2a (SERCA2a) protein.

Certain treatments are greatly enhanced by direct administration of a therapeutic to an organ of the subject via a catheter, for example to the heart by intracoronary injection or infusion. However, individual subjects can vary in their anatomy. A diverse array of catheters are available, each one adapted for use with a specific anatomy. For example, it is known that subjects can have any one of several complex coronary circulatory anatomies, requiring a catheter adapted for a specific coronary anatomy. Such catheters can be constructed from any one of several different types of materials, and may contain internal coatings that differ between catheter types.

To ensure the safety, purity, potency, and effectiveness of new treatments, such as biologies for the prevention, diagnosis, and treatment of human diseases, conditions, or injury, government agencies can require use of a specific delivery device, such as a specific catheter, in the administration of an approved biologic. In the Unites States, biologies are regulated by the Center for Biologies Evaluation and Research, a division of the U.S. Food and Drug Administration Therefore, while a specific catheter may be approved for use with a specific biologic, the diversity of human anatomy may require the use of another catheter adapted for use with a particular anatomy to administer the biologic. Obtaining regulatory approval for each and every catheter that may be used to administer a specific biologic can be prohibitive. In addition, physicians may be accustomed to the use of certain catheters, and prefer to use such catheters in the administration of treatments. Therefore, there is a need for methods, systems and kits that provide consistent administration of a specific biologic to ensure the safety, purity, potency, and effectiveness of the biologic, such as an AAV2/1/SERCA2a vector, and also to provide a delivery system appropriate for an individual's anatomy. For example, intracoronary delivery which is appropriate for an individual's particular coronary anatomy.

Some embodiments of the methods, kits and systems provided herein relate to the use of an infusion catheter for administration, for example intracoronary administration, of a biologic. In some embodiments, the infusion catheter is compatible for use with a specific biologic. For example, the material and/or coating of the surface(s) of the infusion catheter in contact with the biologic (contact surface(s)), e.g. the internal surface of the infusion catheter, may be nonreactive or non-binding to the biologic, or have known level of reactivity or binding. In some embodiments, the infusion catheter can be government-approved for use with a specific biologic. For example, the infusion catheter can have been rigorously tested to provide consistent administration of a biologic to a subject. Some embodiments of the methods, kits and systems provided herein relate to the use of a guide catheter in combination with the infusion catheter. In some embodiments, the guide catheter is selected for use with the particular anatomy of a subject, e.g. the anatomy of the subject's coronary circulation. In some embodiments, the infusion catheter is inserted through the length of the guide catheter, and the biologic administered to the organ of a subject through the lumen of the infusion catheter, so that the biologic does not come in contact with the surfaces of the guide catheter. In this way, the physician can select the guide catheter appropriate for the patient's anatomy, and/or the guide catheter with which the physician is most familiar and comfortable, without needing to determine if the materials of the guide catheter are compatible with the biologic being administered. In some embodiments, the biologic is administered into the lumen of a large vessel of the coronary circulation.

Biologics

Some embodiments of the methods, kits and systems provided herein include the use of biologies. As used herein a biologic can include a medicament manufactured or extracted from a biological source. Examples of biologies include, but are not limited to, antibodies, including fragments and derivatives thereof, vaccines, blood, blood components, somatic cells, tissues, proteins, recombinant therapeutic protein, nucleic acids, and vectors for gene therapy, for example a viral vector. In some embodiments, the biologic comprises a vector for gene therapy, for example a viral vector. In some embodiments, the biologic comprises an adeno-associated virus (AAV) vector. In some embodiments, the biologic comprises a therapeutic polynucleotide encoding a sarcoplasmic/endoplasmic reticulum ATPase 2a (SERCA2a) protein. An example biologic encoding a SERCA2a protein is described in U.S. Pub. No. 2008/0076730, U.S. Pat. Nos. 8,221,738, 8,636,998, and Zsebo K, et al., Circ. Res. 114:101-108, each of which are expressly incorporated by reference in its entirety.

In some embodiments, the biologic is MYDICAR®, MYDICAR® is a recombinant adeno-associated viral (rAAV) vector, which includes an AAV serotype 1 (AAV1) capsid and SERCA2a cDNA flanked by Inverted Terminal Repeats derived from AAV serotype 2 (AAV2). The SERCA2a protein is the only protein expressed after MYDICAR® treatment, and is a fully human, intracellular, endoplasmic protein that is naturally expressed in cardiomyocytes. MYDICAR® can be delivered via antegrade epicardial coronary artery infusion in an outpatient cardiac catheterization laboratory. MYDICAR® therapy restores $Ca^{2+}$ cycling in cardiomyocytes by normalizing SERCA2a protein levels in advanced heart failure patients. In some embodiments, the biologic comprises DNase resistant particles (DRP) of adeno-associated virus serotype 1 (AAV1) vector encoding sarcoplasmic/endoplasmic reticulum ATPase 2a (SERCA2a) protein. In some embodiments, the biologic is delivered in a pharmaceutical carrier, for example saline. In some embodiments, the pharmaceutical carrier comprises a buffer, sodium chloride, L-histidine, magnesium chloride, polysorbate 20, and water.

Subjects

Some embodiments of the methods, kits and systems provided herein include the administration of a biologic, such as an AAV2/1/SERCA2a vector to a subject via a catheter, for example intracoronary administration. In some embodiments, the subject is mammalian, such as human. In some embodiments, the subject has a disease or disorder that may be treated by administration of the biologic, such as an AAV2/1/SERCA2a vector. In some embodiments, the disorder is associated with heart failure. In some embodiments, the disorder is a cardiomyopathy, such as an ischemic cardiomyopathy or a non-ischemic cardiomyopathy. In some embodiments, the subject has advanced heart failure with systolic dysfunction. In some embodiments, the subject has symptoms of heart failure that may be identified with the New York Heart Association (NYHA) functional classification. Classes in the NYHA classification include: Class I: cardiac disease, but no symptoms and no limitation in ordinary physical activity, e.g. no shortness of breath when walking, climbing stairs; Class II: mild symptoms (mild shortness of breath and/or angina) and slight limitation during ordinary activity; Class III: marked limitation in activity due to symptoms, even during less-than-ordinary activity, e.g. walking short distances (20-100 m), comfortable only at rest, and Class IV: severe limitations, experiences symptoms even while at rest, mostly bedbound patients. In some embodiments, a subject can have NYHA class III/IV symptoms of heart failure. In some embodiments, the subject lacks antibodies, such as neutralizing antibodies, to the biologic. In some embodiments, the subject lacks neutralizing antibodies to a gene therapy vector, such as an AAV vector, such as an AAV2/1/SERCA2a vector.

Infusion Catheters

Some embodiments of the methods, kits and systems provided herein include the use of infusion catheters. An infusion catheter can include a proximal end and a distal end, and a lumen. The distal end of the infusion catheter is inserted into a subject, and delivers a biologic to the subject, for example, into one or more coronary arteries or veins. In some embodiments, the infusion catheter is compatible with administration of a biologic, for example an AAV vector, to a subject. For example, the surface or surfaces of the infusion catheter (and other delivery devices described herein, for example but not limited to, syringes, tubing, stopcocks) which come in contact with the biologic (contact surface(s)), e.g. the surfaces of the lumen, and/or around the distal tip of the infusion catheter, are non-reactive or non-binding to the biologic, or have a known level of reactivity or binding to the biologic. In some embodiments the reactivity or binding to the biologic is evaluated to determine if the contact surfaces of the infusion catheter and other delivery devices described herein are compatible with the biologic. For example, a certain level of interaction with the biologic may deemed acceptable depending on the biologic being administered. In some embodiments it may be acceptable to have a level of loss of the biologic due to binding (adsorption) and/or degradation when administered through the infusion catheter and/or and other delivery devices described herein where the amount of loss is, is about, or is not more than, 15%, 10%, 5%, 4%, 3%, 2% 1%, 0.5% or 0.01%, or a range defined by any two of these values. In a preferred embodiment, less than 1%, 0.5% or 0.01% of the biologic is lost due to interaction with the infusion catheter and/or and other delivery devices described herein, e.g. by binding and/or degradation. In some, embodiments, the infusion catheter has government-approval for use with a specific biologic.

Some embodiments provided herein include determining if an infusion catheter and/or and other delivery devices described herein are compatible with a biologic. In some embodiments, determining can include measuring or otherwise determining (e.g. through review of literature or specifications for the contact surface material) the binding (e.g. adsorption, and/or absorption), and/or degradation of the biologic to a contact surface of the infusion catheter and/or other delivery devices described herein. In some embodiments the contact surface may result in the loss of (e.g. through adsorption, absorption and/or degradation), less than 15%, 10%, 5%, 4%, 3%, 2% 1%, 0.5%, 0.01%, or 0.001% or a range defined by any two of these values of a dose of the biologic. In some embodiments, compatibility is determined by the level of loss of the biologic (e.g. through adsorption, absorption and/or degradation) being below a pre-determined level. In some embodiments, the pre-determined level of loss (e.g. through adsorption, absorption and/or degradation) acceptable for compatibility of the contact surface is less than 15%, 10%, 5%, 4%, 3%, 2% 1%, 0.5%, 0.01%, or 0.001% or a range defined by any two of these values of a dose of the biologic. In some of the embodiments, a dose of a biologic can comprise or can consist of a pharmaceutically effective amount of the biologic.

In some embodiments, an infusion catheter, including any of the embodiments described herein, may be used with any one of a plurality of different guide catheters. Infusion catheters can be inserted into a guide catheter through the length of a lumen of a guide catheter during administration of a biologic to a subject.

In some embodiments, the external diameter of the infusion catheter is small enough to fit within a lumen of a guide catheter. In some embodiments, the external diameter of an infusion catheter is such that when the infusion catheter is inserted along the length of the lumen of a guide catheter, sufficient space remains between the external wall of the infusion catheter and the inside wall of the lumen of the guide catheter to permit fluids or gas to flow within such space. For example, in some embodiments radiopaque fluids may be flushed through the space that remains between the external wall of the infusion catheter and the inside wall of a lumen of the guide catheter to visualize the location of the distal tip of the guide catheter and/or the infusion catheter. In some embodiments, the external diameter of an infusion catheter, or the tip of the infusion catheter, can be in the range from about 0.5 French to about 10 French. In some embodiments, the external diameter of an infusion catheter, or the tip of the infusion catheter, can be in the range from about 1.26 French to about 5 French. In some embodiments, the external diameter of the infusion catheter, or the tip of the infusion catheter, is, is about, or is less than 0.5 inches, 0.4 inches, 0.3 inches, 0.275 inches. 0.250 inches, 0.236 inches, 0.220 inches, 0.2 inches or a range defined by any two of these values. In some embodiments, the diameter of the lumen of the infusion catheter is sufficient for a fluid comprising the biologic to flow through the lumen during administration of the biologic, preferably without backpressure. In some, embodiments, the lumen of the infusion catheter, for example at the distal end, has a diameter in the range from about 0.010 inches to about 0.040 inches. In some, embodiments, the lumen of the infusion catheter, for example at the distal end, has a diameter in the range from about 0.16 inches to about 0.75 inches. In some embodiments, the minimum diameter of the lumen of the infusion catheter is not less than 0.20 inches, 0.19 inches, 0.18 inches, 0.17 inches, 0.16 inches, 0.15 inches, 0.14 inches, 0.13 inches, 0.12 inches, 0.11 inches, 0.10 inches or a range defined by any two of these values. In some embodiments, the surfaces of the infusion catheter which come in contact with the biologic, e.g. the surface of the lumen and the distal tip, are coated with a hydrophilic material, or a hydrophobic material, or a material known to be compatible with the biologic administered through the infusion catheter.

In some embodiments, an infusion catheter can comprise any one of several different forms of construction, for example, the construction of an infusion catheter can include stainless steel braided; stainless steel braid. PTFE; non-tapered, stainless steel braid, PTFE; tapered, stainless steel braid, PTFE; coiled stainless steel, PTFE, PEBAX; vortec plus braiding: fiber and platinum braid; vortec fiber and stainless steel braid; vortec fiber braiding; TFE shaft with hydrophilic coating; braid/coil design; stainless steel braid/stainless steel coil; braided stainless steel, PTFE, PEBAX; nylon ribbon braiding; stainless steel braid; nitinol coil reinforced with several extrusion zones; non-braided (RX); braided, hydrophilic; braided; hydrophilic; tungsten coil, PTFE liner; dual-lumen (RX and OTW); stainless steel microwire wind, spray-coated plastic. In some embodiments, the construction of an infusion catheter can include stainless steel braided; coiled stainless steel; vortec fiber braiding; nylon ribbon braiding; or stainless steel microwire wind. In some embodiment, the infusion catheter includes a contact surface which may be contacted with a biologic. In some embodiments the contact surface of the infusion catheter, and/or other contact surfaces utilized in the methods and kits disclosed herein, are made from, and/or coated with a material selected from one or more of the following, or combinations thereof: polyurethane, polypropylene, polyvinyl chloride, polytetrafluoroethylene (Teflon®), nylon, polyurethane, nylon/polyurethane, polyethylene terephthalate stainless steel, polyether block amides (Pebax®), and thermoplastic rubber (Santoprene). In some embodiments, the contact surface of the infusion catheter is made from, and/or coated with a material selected from one or more of the following, or combinations thereof: polyurethane, polypropylene, polyvinyl chloride, polytetrafluoroethylene (Teflon®), nylon, polyurethane, nylon/polyurethane, polyethylene terephthalate stainless steel, polyether block amides (Pebax®), and thermoplastic rubber (Santoprene). In some embodiments, other surfaces that may come into contact with the biologic utilized in the methods and kits disclosed herein, are made from, and/or coated with a material selected from one or more of the following, or combinations thereof: polyurethane, polypropylene, polyvinyl chloride, polytetrafluoroethylene (Teflon®), nylon, polyurethane, nylon/polyurethane, polyethylene terephthalate stainless steel, polyether block amides (Pebax®), and thermoplastic rubber (Santoprene).

Examples of infusion catheters that may be useful with embodiments of the methods, kits, and systems provided herein include microcatheters. Examples of microcatheters include: Asahi Corsair (Asahi Intecc USA, Inc.); Usher, MicroSheath (Nontapered), MicroSheath (Tapered) (Bard Peripheral Vascular, Inc.); ProTrack Microcatheter, ProTrack Microcatheter (Baylis Medical Company. Inc.); Renegade Hi-Flo Microcatheter, Renegade Hi-Flo Fathom Preloaded System, Renegade Hi-Flo Fathom Kit, Renegade Hi-Flo Transend Kit, Renegade STC 18 Microcatheter, Renegade Microcatheter, FasTracker 325 Microcatheter, FasTracker 325 Pre-Loaded System (Boston Scientific Corporation); Prowler Select LP-ES, Prowler Select Plus, Prowler 10, Prowler 14, Prowler Plus, Transit Microcatheters, Rapidtransit Microcatheters, Courier 170 Microcatheters, Courier 190 Microcatheters (Codman Neurovascular); Cantata 2.5, Cantata 2.8 (Cook Medical); Marksman 27 (Covidien); Maestro, Maestro, EmboCath Plus (Merit Medical Systems, Inc.); PX400, PX Slim, Velocity (Penumbra, Inc.); Proxis Infusion Catheter (St. Jude Medical, Inc.); Excelsior 1018, Excelsior SL-10, Excelsior XT-27, Merci Microcatheter 14X and 18L, Neuro Renegade Hi-Flo, Tracker Excel-14, FasTracker-10, FasTracker-18 MX, Renegade 18 (Stryker Neurovascular); Progreat Q, Progreat 2.7. Progreat 2.4, Progreat Q Coaxial Microcatheter System, Progreat Coaxial Microcatheter System (Terumo Interventional Systems); Twin-Pass Dual Access Catheter, Twin-Pass 0.023 Dual Access Catheter, Supercross Microcatheter, Supercross Angled Tip Microcatheter (Vascular Solutions, Inc.); and Valet (Volcano Corporation). More examples of microcatheters that may be useful with embodiments of the methods, kits, and systems provided herein include: Cantata® 2.9 Microcatheter (Cook); VIA Microcatheter (Sequent Medical); Reverse Medical Microcatheter-027 (Reverse Medical Corporation), Modified Concentric Microcatheter (Concentric Medical); CXI Support Catheter (Cook); Orion Micro Catheter (Micro Therapeutics); Excelsior® XT-27™ Microcatheter (Stryker Neurovascular); Marksman Catheter (EV3); Headway 27 Microcatheter (MicroVention, Inc); and Finecross MG Coronary Micro-Guide Catheter (Terumo Corporation).

Guide Catheters

Some embodiments of the methods, kits and systems provided herein include the use of guide catheters. In some embodiments, the guide catheter comprises a lumen having sufficient diameter such that an infusion catheter as described herein can be inserted through the length of a lumen of the guide catheter. In some embodiments, a guide catheter is selected for the particular anatomy of a subject, for example the anatomy of the subject's coronary circulation. In some embodiments, a guide catheter may lack government approval for use with a specific biologic. In other words, use of the guide catheter, without the combined use of a government-approved infusion catheter, may lack government approval for administration of a specific biologic to a subject. In some embodiments, the surface material of the guide catheter, for example lumen(s) of the guide catheter has not been determined to be compatible with the biologic (e g. as compatibility is described herein for the infusion catheter). In some embodiments, the surface material of the guide catheter, for example lumen(s) of the guide catheter, is not compatible with the biologic, or is at least 50%, 100%, or 200% less compatible with the biologic as compared to the contact surface of the infusion catheter.

In some embodiments, a guide catheter is adapted for intracoronary delivery of the distal end of an inserted infusion catheter, in which the subject has a coronary anatomy such as non-obstructive or non-occlusive, with right or co-dominance; occluded right coronary artery, patent left coronary artery, left to right collaterals, with right or co-dominance; occluded left anterior descending artery, patent left circumflex artery, right to left collaterals from right coronary artery to left anterior descending artery, with right or co-dominance; occluded left circumflex artery, patent left anterior descending artery, right to left collaterals to left circumflex artery from right coronary artery, with right or co-dominance; left dominant circulation, with left dominance; short or non-existent left main coronary artery such that the anatomy allows for an operator to cannulate both the left anterior descending artery and left circumflex artery with a single or combination of catheters, with right dominance; and short or non-existent left main coronary artery such that the anatomy allows for an operator to cannulate both the left anterior descending artery and left circumflex artery with a single or combination of catheters, with left dominance. In some embodiments, the subject has a coronary anatomy such as non-obstructive or non-occlusive; occluded right coronary artery; occluded left anterior descending artery; occluded left circumflex artery; left dominant circulation; short or non-existent left main coronary artery with right dominance; and short or non-existent left main coronary artery with left dominance. In some embodiments, the guide catheter is selected for intracoronary delivery of the distal end of an inserted infusion catheter to a left coronary artery, a right coronary artery, a left anterior descending artery, a left circumflex artery, a saphenous vein graft, or a left internal mammary artery graft.

Administration of a Biologic

Some embodiments provided herein include methods for providing consistent administration of a biologic (e.g., one or more of the exemplary biologies disclosed herein), such as an AAV vector, to a plurality of subjects, in which the plurality of subjects comprise diverse anatomies. In some embodiments, administration is intracoronary administration to a plurality of subjects, where the subjects comprise diverse coronary circulatory anatomies. Some embodiments include obtaining an embodiment of an infusion catheter described herein. In some embodiments the infusion catheter has proximal and distal ends, wherein the infusion catheter is adapted for specific use in the intracoronary administration of the biologic. In some embodiments, the infusion catheter can be adapted for specific use in the intracoronary administration of the biologic by including a contact surface that is compatible with the biologic. In some embodiments, obtaining an embodiment of an infusion catheter described herein can also include determining an infusion catheter is compatible with the biologic. In some embodiments, obtaining an embodiment of an infusion catheter described herein can also include selecting an infusion catheter that is known to be compatible with the biologic. In some embodiments, the contact surface of the infusion catheter is compatible with the biologic. In some embodiments, the infusion catheter is government-approved for specific use in the administration of the biologic. In some embodiments, the particular type of infusion catheter is government-approved for use in the administration of the biologic. In some embodiments, the particular brand of infusion catheter is government-approved for use in the administration of the biologic. In some embodiments, an infusion catheter comprising particular materials is government-approved for use in the administration of the biologic. In some embodiments, an infusion catheter comprising a lumen having a particular material and/or coating is government-approved for use in the administration of the biologic.

In some embodiments, the infusion catheter is adapted for insertion into any one of a plurality of different guide catheters as described herein. In other words, the infusion catheter can be inserted through the length of any one of several different guide catheters. In some embodiments, the different guide catheters are adapted for delivery of the distal end of the infusion catheter to different locations within the heart, for example the coronary circulation. In some embodiments, the different guide catheters are adapted to navigate through different coronary anatomies of different subjects. Some embodiments include selecting a guide catheter for use in the delivery of the distal end of an infusion catheter during the intracoronary administration of a biologic to a subject having a particular coronary anatomy.

Some embodiments include extending the infusion catheter through the length of a lumen of the guide catheter such that the distal end of the infusion catheter is flush with the distal end of the guide catheter when the biologic is delivered to the subject. In some embodiments, the distal end of the infusion catheter is extended beyond the distal end of the guide catheter when the biologic is delivered to the subject. In some embodiments, the distal end of the infusion catheter extends beyond the distal end of the guide catheter when the biologic is delivered to the subject by a distance of, of about, or not more than, 1 inch, 2 inches, 3 inches, 4 inches, 5 inches, 6 inches, 7 inches, 8 inches, 9 inches, or 10 inches, or a range defined by any two of these values. In some embodiments, the distance is between 0 inches and 8 inches, or between 0 and 4 inches. In some embodiments, the infusion catheter is extended through the length of a lumen of the guide catheter prior to insertion of the guide catheter into the subject. In some embodiments, the infusion catheter is extended through the length of a lumen of the guide catheter after insertion of the guide catheter into the subject. In some embodiments, the infusion catheter is extended through the length of a lumen of the guide catheter during insertion of the guide catheter into the subject. In some embodiments, the distal end of the guide catheter is navigated to the lumen of a large blood vessel of the heart to deliver the distal end of the infusion catheter. In some embodiments, a large blood vessel of the heart can include one or more of an artery or vein selected from: a left coronary artery, a right coronary artery, a left anterior descending artery, a left circumflex artery, a saphenous vein graft, or a left internal mammary artery graft. In some embodiments, the blood pressure at the distal end of the guide catheter is measured. In some embodiments, the location of the distal end of the guide catheter can be determined. In some embodiments, the tip of the guide catheter and/or the infusion catheter can be radiopaque. In some embodiments, a radiopaque dye is flushed through the guide catheter lumen external to the infusion catheter lumen, and from the distal end of the guide catheter. In some embodiments, infusions can occur with continuous monitoring of catheter tip pressure to verify patient hemodynamic stability and to recognize catheter tip occlusion of a coronary orifice. The ability to confirm selective engagement of the coronary artery with brief contrast injections during infusion is advantageous to determine selective delivery of the therapeutic agent.

Some embodiments include administering a biologic, for example, an AAV vector, or an AAV2/1/SERCA2a vector, to cardiac tissue of the subject through the lumen of the infusion catheter. Embodiments of the administration of a biologic useful with the methods, kits and systems provided herein can be found in U.S. Pub No. 2008/0076730, U.S. Pat. Nos. 8,221,738, 8,636,998, and Zsebo K., et al., Circ. Res. 114:101-108 which are each incorporated by reference herein in its entirety. In some embodiments, the distal end of the infusion catheter is extended from the distal end of the guide catheter during administration of the biologic.

In some embodiments, during administration of the biologic, the lumen of the infusion catheter is in fluid communication with a delivery device selected from the group consisting of a syringe, a stopcock, a manifold, an infusion pump, sterile tubing, and an infusion line, wherein a surface of the delivery device contacting the biologic is adapted for specific use with the biologic. In some embodiments, the contact surface(s) of the delivery device(s) are made from, and/or coated with, the same material as the contact surface of the infusion catheter. In some embodiments, the materials are different.

Some embodiments also include intravenous administration of a vasodilating substance to the subject. In some embodiments, the vasodilating substance can include a NO increasing substance. In some embodiments, the vasodilating substance is nitroglycerin. Embodiments useful with the methods, kits and systems provided herein that include administration of nitroglycerin can be found in U.S. Pat. Nos. 8,221,738, and 8,636,998 which are each incorporated by reference herein in its entirety. In some embodiments, the nitroglycerin is administered to the subject prior to administration of the biologic to the subject. In some embodiments, the nitroglycerin is administered to the subject prior to administration of the biologic for a period of at least 1 minute, 5 minutes, 10 minutes, 20 minutes 30 minutes, or a period in the range between any two of the foregoing numbers. In some embodiments, the nitroglycerin is administered to the subject during administration of the biologic.

Systems and Kits

Some embodiments provided herein include kits and systems for providing consistent administration of a biologic to an organ of a subject or a plurality of subjects via an infusion catheter as described herein. In some embodiments, the kit or system comprises a biologic and infusion catheter, as described herein. Some such embodiments include a kit comprising a biologic, such as an AAV vector, for example an AAV2/1/SERCA2a vector, and an infusion catheter as described herein adapted for use in the intracoronary administration of the biologic included in the kit. In some embodiments, the infusion catheter is adapted for insertion into any one of a plurality of guide catheters as described herein, wherein each guide catheter of the plurality is adapted for a different anatomy. Some embodiments also include a guide catheter adapted for the coronary anatomy of a subject. Some embodiments include a comprising a biologic, such as an AAV2/1/SERCA2a vector, and a plurality of guide catheters, wherein each guide catheter is adapted for a different coronary anatomy of a subject; and an infusion catheter adapted for insertion into each of the plurality of guide catheters, and adapted for specific use in the intracoronary administration of the biologic to a subject. Some embodiments of the foregoing kits and systems can also include a delivery device selected from the group consisting of a syringe, a stopcock, a manifold, an infusion pump, sterile tubing, and an infusion line, wherein a surface of the delivery device that contacts the biologic during administration is adapted for specific use with the biologic. In some embodiments, the contact surface(s) of the delivery device(s) are made from, and/or coated with, the same material as the contact surface of the infusion catheter. In some embodiments, the materials are different.

In some embodiments, the kit or system can include a stock amount of the biologic, such as an AAV2/1/SERCA2a vector, and a carrier solution for dissolving or diluting the stock amount. In some embodiments, the kit or system can a stock amount of the vasodilator(s), including but not limited to NO increasing substance(s), and a carrier solution for dissolving or diluting the stock amount. In some embodiments, the kit contains a container with a mixture of the therapeutic agent and the amount of vasodilating substance(s). The stock amounts of the therapeutic agent and/or vasodilating substance(s) can be in dry form requiring dissolution or mixing in a carrier solution, a concentrated solution requiring dilution, or in a form ready for administration to the patient without additional preparation. In some embodiments, the kit includes one or more intravascular infusion or injection catheters for intracoronary administration of the vasodilating substance(s) and/or therapeutic agent. In some embodiments, the biologic is lyophilized. In some embodiments, the kit or system can also include a diluent compatible with the biologic.

EXAMPLES

Example 1

Administration of an AAV2/1/SERCA2a Vector

A subject having NYHA class III/IV symptoms of heart failure is examined, and a guide catheter is selected that is appropriate for the subject's coronary anatomy and for the delivery of a distal end of an infusion catheter inserted along the length of the lumen of the guide catheter to a large blood vessel of the coronary circulation.

An infusion catheter is inserted along the length of the lumen of the selected guide catheter.

A sterile solution comprising the AAV2/1/SERCA2a vector is prepared. A syringe containing the sterile solution is loaded into a syringe pump. The syringe pump is attached to an infusion line, stopcock and the lumen of the infusion catheter.

The guide catheter compatible with the AAV2/1/SERCA2a is inserted into the subject and the distal end of the guide catheter engages with the lumen of a target large blood vessel of the coronary circulation.

The subject is intravenously administered nitroglycerin for at least ten minutes prior to administration of a solution comprising an AAV2/1/SERCA2a vector. The distal end of the infusion catheter is extended from the distal end of the guide catheter and into the lumen of the large blood vessel. The sterile solution is administered to the subject.

Example 2

Kit for Consistent Administration of MYDICAR®

A kit for providing consistent intracoronary administration of a biologic to a subject of a plurality of subjects, wherein the plurality of subjects comprise diverse coronary anatomies can include: a vial containing MYDICAR®; and an infusion catheter which has contact surfaces including the lumen and distal end of the infusion catheter that are compatible MYDICAR®. The contact surfaces of the infusion catheter are non-reactive with MYDICAR®. The infusion catheter is government approved for use in the administration of MYDICAR to a patient. The infusion catheter has dimensions such that it can be inserted into any one of several different guide catheters, each guide catheter adapted for navigation within a different coronary anatomy between patients.

Example 3

Administration of a Biologic

A subject requiring treatment with a biologic is examined, and a guide catheter is selected that is appropriate for the subject's anatomy and for the delivery of a distal end of an infusion catheter inserted along the length of the lumen of the guide catheter to the site of infusion of the biologic.

An infusion catheter compatible with the biologic is inserted along the length of the lumen of the selected guide catheter.

A syringe containing pharmaceutical composition comprising the biologic is prepared, and is attached to an infusion line, stopcock and the lumen of the infusion catheter. Optionally, the syringe can be loaded into a syringe pump.

The guide catheter is inserted into the subject and the distal end of the guide catheter is advanced to the site of the infusion.

The distal end of the infusion catheter is extended from the distal end of the guide catheter to the site of infusion. The composition is administered to the subject.

Example 4

Kit for Consistent Administration of a Biologic

A kit for providing consistent intracoronary administration of a biologic to a subject of a plurality of subjects, wherein the plurality of subjects comprise diverse anatomies of anatomical structures needed to reach the site of injection with a catheter can include: a vial containing the biologic, and an infusion catheter which has contact surfaces including the lumen and distal end of the infusion catheter that are compatible or non-reactive with the biologic. In some embodiments, the infusion catheter is government approved for use in the administration of the biologic to a patient. The infusion catheter has dimensions such that it can be inserted into any one of several different guide catheters, each guide catheter adapted for navigation within a different anatomy between patients.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method for providing consistent intracoronary administration of a biologic to a plurality of subjects having diverse coronary anatomies using multiple types of guide catheters and a single type of biologic-compatible infusion catheter, the method comprising:
(a) obtaining a plurality of kits, each kit comprising:
   (i) an infusion catheter having proximal and distal ends, wherein the infusion catheter is adapted for use in the intracoronary administration of a biologic to a subject, and wherein a contact surface of the infusion catheter comprises a material that is compatible with the biologic; and (ii) a container comprising the biologic, wherein the infusion catheter and biologic in each kit of the plurality of kits are materially identical;

(b) obtaining a first guide catheter having proximal and distal ends, wherein the first guide catheter is adapted for the coronary anatomy of a first subject selected from a plurality of subjects comprising diverse coronary anatomies;

(c) inserting the distal end of first guide catheter into a coronary artery or vein of the first subject;

(d) advancing the infusion catheter of a first kit of the plurality of kits longitudinally within the lumen of the first guide catheter to position the distal end of the infusion catheter flush with or extending beyond the distal end of the first guide catheter; and (e) administering the biologic of the first kit of the plurality of kits to cardiac tissue of the first subject through the lumen of the infusion catheter of the first kit of the plurality of kits, wherein the infusion catheter of the first kit of the plurality of kits and the first guide catheter are configured such that following step (c), the infusion catheter can be moved longitudinally within the lumen of the guide catheter;

(f) obtaining a second guide catheter having proximal and distal ends, wherein the second guide catheter is adapted for the coronary anatomy of a second subject selected from a plurality of subjects comprising diverse coronary anatomies, wherein the coronary anatomy of the second subject and second guide catheter are each different from the first guide catheter and the coronary anatomy of first subject of step (b);

(g) inserting the distal end of second guide catheter into a coronary artery or vein of the second subject;

(h) advancing the infusion catheter of a second kit of the plurality of kits longitudinally within the lumen of the second guide catheter to position the distal end of the infusion catheter flush with or extending beyond the distal end of the second guide catheter; and (i) administering the biologic of the second kit of the plurality of kits to cardiac tissue of the second subject through the lumen of the infusion catheter of the second kit of the plurality of kits, wherein the infusion catheter of the second kit of the plurality of kits and the second guide catheter are configured such that following step (g), the infusion catheter can be moved longitudinally within the lumen of the guide catheter.

2. The method of claim 1, wherein the infusion catheter of each kit of the plurality of kits is adapted for insertion into any one of a plurality of different guide catheters; and wherein each guide catheter of the plurality is adapted for a different coronary anatomy of a subject.

3. The method of claim 1, wherein the coronary anatomy of the first and/or second subject is selected from the group consisting of: non-obstructive or nonocclusive; occluded right coronary artery; occluded left anterior descending artery; occluded left circumflex artery; left dominant circulation; short or non-existent left main coronary artery, with right dominance; and short or non-existent left main coronary artery, with left dominance.

4. The method of claim 1, wherein the first and/or second guide catheter is adapted for delivery of the distal end of the infusion catheter to a left coronary artery, a right coronary artery, a left anterior descending artery, a left circumflex artery, a saphenous vein graft, or a left internal mammary artery graft.

5. The method of claim 1, wherein the first and/or second guide catheter is selected from the group consisting of diagnostic catheter, guide angiographic catheter for selective arterial engagement, guide angiographic catheter for selective venous engagement, and guide angiographic catheter for selective bypass graft engagement.

6. The method of claim 1, wherein each infusion catheter of the plurality of kits has an external diameter in the range from about 0.5 French to about 10 French, and wherein the lumen at the distal end of each of the infusion catheters of the plurality of kits has a diameter in the range from about 0.010 inches to about 0.040 inches.

7. The method of claim 1, further comprising intravenous administration of nitroglycerin to the first and/or second subject.

8. The method of claim 7, wherein the nitroglycerin is administered to the subject for a period of at least 10 minutes prior to administration of the biologic.

9. The method of claim 1, wherein the biologic is administered into the lumen of a blood vessel of the coronary circulation in vivo.

10. The method of claim 1, wherein the biologic is administered at a rate of about 0.1 ml/min to about 20 ml/min.

11. The method of claim 1, wherein the biologic comprises a vector for gene therapy.

12. The method of claim 1, wherein the biologic comprises an adeno-associated virus (AAV) vector.

13. The method of claim 1, wherein the biologic comprises a therapeutic polynucleotide encoding a sarcoplasmic/endoplasmic reticulum ATPase 2a (SERCA2a) protein.

14. The method of claim 1, wherein the biologic comprises less than or equal to about $2.5 \times 10^{14}$ DNase resistant particles (DRP) adeno-associated virus serotype 1 (AAV1) vector encoding sarcoplasmic/endoplasmic reticulum ATPase 2a (SERCA2a) protein.

15. The method of claim 1, wherein the first and second subject lacks AAV1 neutralizing antibodies; and wherein the subject has New York Heart Association (NYHA) class III/IV symptoms of heart failure.

16. The method of claim 1, wherein the subject is human.

17. The method of claim 1, wherein (d) is performed after (c).

18. The method of claim 1, wherein (c) is performed after (d).

19. The method of claim 1, further comprising (j) inserting the distal end of the infusion catheter of the first and/or second kit of the plurality of kits into the proximal end of the first and/or second guide catheter, respectively, and advancing the distal end of the infusion catheter into the lumen of the guide catheter.

20. The method of claim 19, wherein (c) and/or (g) is performed prior to (j).

21. The method of claim 19, wherein (j) is performed prior to (c) and/or (g).

22. The method of claim 1, further comprising flushing a fluid or gas through the first and/or second guide catheter lumen external to the infusion catheter lumen.

23. The method of claim 22, wherein the fluid is a radiopaque fluid.

24. The method of claim 1, wherein each infusion catheter of each of the plurality of kits is government approved specifically for use with the biologic.

25. The method of claim 24, wherein the biologic comprises an adeno-associated virus (AAV) vector encoding a sarcoplasmic/endoplasmic reticulum ATPase 2a (SERCA2a) protein.

26. The method of claim 1, wherein the wherein the contact surface material of each of the infusion catheters has a binding level of the biologic less than 1% of a dose of the biologic.

* * * * *